United States Patent [19]

Finlan et al.

[11] Patent Number: 5,035,863

[45] Date of Patent: Jul. 30, 1991

[54] SURFACE PLASMON RESONANCE SENSORS

[75] Inventors: Martin F. Finlan; Michael A. W. Brady, both of Buckinghamshire, England

[73] Assignee: Amersham International plc, Buckinghamshire, United Kingdom

[21] Appl. No.: 350,033

[22] Filed: May 10, 1989

[30] Foreign Application Priority Data

May 10, 1988 [GB] United Kingdom ............... 8811053
May 10, 1988 [GB] United Kingdom ............... 8811054
Sep. 12, 1988 [GB] United Kingdom ............... 8821336

[51] Int. Cl.$^5$ ............... G01N 21/00; G01N 21/55; G01N 33/559; G01J 3/30

[52] U.S. Cl. ............... 422/82.05; 422/68.1; 422/82.09; 356/318; 356/445; 436/515; 436/516

[58] Field of Search ............... 422/82.05, 82.11; 356/318, 445; 436/515, 516

[56] References Cited

U.S. PATENT DOCUMENTS

| | | | |
|---|---|---|---|
| 4,244,797 | 1/1981 | Aladjem et al. | 436/515 |
| 4,810,658 | 3/1989 | Shanks et al. | 422/82.08 |
| 4,844,613 | 7/1989 | Batchelder et al. | 356/445 |
| 4,889,427 | 12/1989 | Van Veen et al. | 356/445 |
| 4,909,990 | 3/1990 | Block et al. | 422/82.11 |
| 4,931,384 | 6/1990 | Layton et al. | 356/318 |

FOREIGN PATENT DOCUMENTS

| | | |
|---|---|---|
| 2458605 | 6/1976 | Fed. Rep. of Germany . |
| 2558262 | 7/1985 | France . |
| 2155176 | 9/1985 | United Kingdom . |
| 2173895 | 10/1986 | United Kingdom . |

OTHER PUBLICATIONS

"Surface Plasmon Resonance For Gas Detection and Biosensing", Liedberg et al. *Sensors and Actuators*, vol. 4, 1983, pp. 299-304.

"Instantaneous Observation of Angular Scan-Attenuated Total Reflection Spectra", K. Oda and M. Fukui, *Optics Communications*, vol. 59, Nos. 5, 6, pp. 361-365.

"Surface Plasmon Microscopy", E. Yeatman and E. A. Ash, *Electronics Letters*, vol. 23, No. 20, Sep. 1987, pp. 1091-1092.

*Primary Examiner*—Robert J. Warden
*Assistant Examiner*—Theresa A. Trembley
*Attorney, Agent, or Firm*—Wenderoth, Lind & Ponack

[57] ABSTRACT

A surface plasmon resonance (SPR) sensor is adapted for biochemical and similar testing on large area samples such as the gel of an electrophoresis apparatus. The gel is sandwiched between a pair of plates. One of the plates is of transparent material and, sandwiched between itself and the gel is a metal layer of a mosaic of silver dots. Light from a source is directed via a reflector and undergoes total internal reflection at the interfacce between the transparent plate and metal layer. The reflected light is passed via another reflector to a light detector. The equipment is arranged so that SPR occurs at the metal layer, which resonance is critically dependent upon the refractive index of the gel. The structure including the light source and detector, together with reflectors is caused to scan across the gel surface to enable a two-dimensional representation of the changes in refractive index across the gel to be built up. This enables the progress of sequencing to be monitored.

49 Claims, 5 Drawing Sheets

SURFACE PLASMON RESONANCE SENSORS

BACKGROUND OF THE INVENTION

This invention relates to surface plasmon resonance (SPR) sensors for use in biological, biochemical and chemical testing. The invention is particularly concerned with adaptions of such sensors to enable larger areas to be covered and thus enable the SPR technique to be used, for example, in applications such as sequencing.

Sequencing of macromolecules, for example nucleic acids such as DNA, is usually carried out by biochemical fragmentation, followed by gel electrophoresis. Following electrophoresis, the sequence is detected by exposure of the gel to autoradiographic film to give a two-dimensional picture from which the sequence of individual nucleotide bases can be read. There are currently two main techniques used for fragmentation, the Maxam-Gilbert method involving the cleavage of DNA molecule by a two-stage addition of chemicals, and the Sanger method involving the preparation of separate samples of dideoxynucleotide of each of the four bases C, G, A and T and then the growth of a complementary DNA strand to that of the DNA under test using an enzyme. Both techniques end up with four different sub-samples, enabling identification of the four bases, each containig fragments of different lengths. A radioactive or fluorescent label is attached to each fragment to enable detection of the sequence using autoradiography. In electrophoresis, the four different sub-samples, containing respective sets of labelled fragments are each placed in a separate well and thus generate a separate and distinct track across the gel as the electrophoresis proceeds. After the electrophoresis has finished, the gel is separated and typically dried and is then, in the case of the radioactive label, exposed to autoradiographic film to obtain an image of the pattern of labelled fragments of different length and belonging to different nucleotide groups.

Autoradiography, while it can offer good sensitivity and resolution is an inconvenient technique, taking considerable skill to achieve good results, and is a fairly lengthly procedure, requiring many hours or even several weeks of exposure. Furthermore, separation of the gel after electrophoresis can lead to damage unless great care is taken, and the very necessary drying of the gel prior to exposure is also tricky since shrinking of the gel must be avoided if meaningful results are to be obtained.

In the present invention, the requirement for autoradiography is eliminated by enabling direct monitoring of the gel using a surface plasmon resonance (SPR) detector. The SPR detector operates to detect changes in the refractive index of the gel across the gel surface. Areas of the gel where fragments are present will have a different refractive index to those where they are not and a "picture" of the gel surface can thus be built up. Although the use of gel will be assumed in this specification, the technique can in fact be used with gel-less and other forms of capillary electrophoresis.

Monitoring can be in "real time"—i.e. as the electrophoresis test proceeds, or can be carried out on the gel after electrophoresis has been completed. In this latter case it may be advantageous to expose the gel to air after electrophoresis has finished so that the gel shrinks and thus concentrates the fragments into a smaller area which can be examined by the SPR detector.

The use of surface plasmon resonance in connection with biosensors has been described in detail in our copending European patent application Nos. 0305109 and 89300544.7, together with our copending British patent application Nos. 8811053.1, 8811054.9, 8811919.3 and 8813307.9.

All of the techniques described in these applications can be applied to the teaching of the present invention.

Surface plasmon resonance is the oscillation of the plasma of free electrons which exists at a metal boundary. These oscillations are affected by the refractive index of the material adjacent the metal surface and it is this that forms the basis of the sensor mechanism used in the present invention. Surface plasmon resonance may be achieved by using the evanescent wave which is generated when a p-polarized light beam is totally internally reflected at the boundary of a medium, e.g. glass, which has a high dielectric constant. A paper describing the technique has been published under the title "Surface plasmon resonance for gas detection and biosensing" by Lieberg, Nylander and Lundstrom in Sensors and Actuators, Vol. 4, page 299. Illustrated in FIG. 1 of the accompanying drawings is a diagram of the equipment described in this paper. A beam 1 of light is applied from a laser source (not shown) onto an internal surface 2 of a glass body 3. A detector (not shown) monitors the internally reflected beam 4. Applied to the external surface 2 of glass body 3 is a thin film 5 of metal, for example gold or silver, and applied to the film 5 is a further thin film 6 of organic material containing antibodies. A sample 7 containing antigen is brought into contact with the antibody film 6 to thus cause a reaction between the antigen and the antibody. If binding occurs, the refractive index of the layer 6 will change owing to the size of the antibody molecules and this change can be detected and measured using the surface plasmon resonance technique, as will now be explained.

Figure 1:
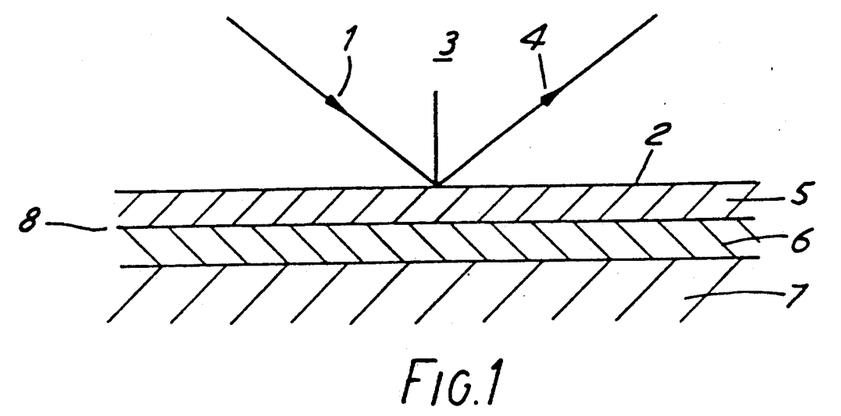
FIG. 1 is a schematic diagram of a known experimental arrangement for demonstrating the surface plasmon resonance effect.

Surface plasmon resonance can be experimentally observed, in the arrangement of FIG. 1, by varying the angle of the incident beam 1 and monitoring the intensity of the internally reflected beam 4. At a certain angle of incidence the parallel component of the light momentum will match with the dispersion for surface plasmons at the opposite surface 8 of the metal film. Provided that the thickness of metal film 5 is chosen correctly there will be an electromagnetic coupling between the glass/metal interface at surface 2 and the metal/antibody interface at surface 8 as a result of surface plasmon resonance, and thus an attenuation in the reflected beam 4 at that particular angle of incidence. Thus, as the angle of incidence of beam 1 is varied, surface plasmon resonance is observed as a sharp dip in the intensity of the internally reflected beam 4 at a particular angle of incidence. The angle of incidence at which resonance occurs is affected by the refractive index of the material against the metal film 5—i.e. the antibody layer 6—and the angle of incidence corresponding to resonance is thus a direct measure of the state of the reaction between the antibody and the antigen. Increased sensitivity can be obtained by choosing an angle of incidence half way down the reflectance dip curve, where the response is substantially linear, at the beginning of the antibody/antigen reaction, and then maintaining that angle of incidence fixed and observing changes in the intensity of the reflected beam 4 with time.

A typical basic detector comprises the following components:

1) A source of electromagnetic radiation, most likely in or near the visible light region;
2) A block of transparent material such as glass on one surface of which is applied a thin film of metal, for example silver or gold, and on which is supported a medium to be tested in such a way that the metal film is sandwiched between the medium and the glass block;
3) Means for directing the electromagnetic radiation from the source into the transparent block in such a way that the radiation is subject to total internal reflection at that surface of the block to which the metal film is applied;
4) A detector for monitoring the intensity of the radiation which is totally internally reflected.

The point of incidence of the incoming beam of radiation defines a small sensitive zone centered around the point. As the refractive index of the medium changes, the angle of incidence at which SPR occurs changes and, for a fixed angle of incidence, this manifests itself as an alteration in the intensity of the totally internally reflected beam, as detected by the detector. A significant improvement in signal/noise ratio can be achieved, however, by monitoring the entirety of the dip resulting from surface plasmon resonance. This may be achieved either by rapidly scanning the incoming beam of radiation across the angles of incidence which result in surface plasmon resonance, such as described in our application No. 8811053.1, or by utilizing the so called "fan beam" as described in our copending European patent application No. 0305109. In a variant of the fan beam, a line point of incidence is formed using a wedge beam, possibly in conjunction with a semicylinder, as described in the aforementioned European patent application.

SUMMARY OF THE INVENTION

The difficulty in the known apparatus is that the sensitive zone centered around the point or line of incidence is very limited in extent and therefore where a large area needs to be monitored, the existing equipment cannot be used. An object of the present invention, therefore is to obviate such a problem by providing means for moving the point or line of incidence to effectively provide two-dimensional coverage of an area. The movement of the point or line is synchronized with the detector so that, at any one instant of time, the detector knows at which point on the area it is looking.

The metal film is assumed to take the form of a continuous layer. However, in certain circumstances, as will be explained later, it may be desirable to divide the metal film into separate isolated areas whose size depends upon the required resolution and the circumstances of use. In a preferred embodiment, the metal film takes the form of a mosaic of mutually isolated metallized dots. The point or line of incidence is moved across said isolated areas, each of which effectively becomes a separate SPR detector.

A two-dimensional area may be covered either by raster scanning of a point of incidence or by one-dimensional scanning of a suitable line of incidence. Scanning may be effected either by a moving mirror system, or by mechanically scanning a first assembly comprising the radiation source, detector and radiation directing means with respect to a second assembly comprising the glass block and metal film in such a way that the point or line of incidence remains always at the interface between the glass block and the metal film. Other variations will be apparent.

It will be seen that, by incorporating these techniques, it is possible to monitor a two dimensional surface of substantial size. A picture of the events within the medium can thus be built up in real time.

In an embodiment of the invention, the medium is an electrophoresis gel forming part of an electrophoresis apparatus. As the fragments proceed through the gel during the process of electrophoresis, the refractive index of the gel changes locally, and this change can be monitored by the apparatus of the present invention. The output signal from the detector is passed to a microcomputer which builds up a pattern of the refractive index variations over the scanned area to follow the progress of the fragments.

The discontinuous metal film effectively provides a plurality of independent sensitive zones which are individually monitored by the SPR detector as it scans with respect to the gel. The nature of these discontinuities will of course depend on the form of scanning used. For two-dimensional raster-type scanning, the metal film takes the form of the aforementioned mosaic of metal, for example silver, dots. Each of these dots will thus effectively supply a pixel of information to build up a complete picture, in real time, of the progress of sequencing.

Such a two-dimensional multi-dot system can simultaneously monitor a plurality of tracks through the gel and can look at the whole gel surface. A minimum of four such tracks is needed to fully characterize a particular DNA sample, but there is no reason why a number of separate samples should not be monitored simultaneously: the number is limited only by the number of sets of four lanes that can be fitted in the scanning width.

Current standards of resolution for such scanners will allow resolution of less than 100 microns which is more than adequate for gel sequencing. Surface plasmon resonance will operate on silver dot sizes of 100 microns diameter or less.

In practice, the mosaic of dots or other discontinuous metal film is covered by a thin insulating layer, for example of polyimide, in order to prevent interaction between individual dots due to the gel which would otherwise be applied directly to the metal film.

In an alternative embodiment of the invention the medium comprises two components of a biological, biochemical or chemical interaction. A first of these components will normally comprise or be attached to the metal film. The second component is an entity within a sample to be tested. For example, the first component could be an antibody attached to the metal layer and the second component a corresponding antigen within a sample. In general, however, any sensitive material, whether specific or non-specific may be attached to the metal layer for interaction with a corresponding entity in the sample. Indeed, the metal layer itself may in some circumstances act as the first component since this will act as a non-specific sensitive material with which certain classes of entity within a sample may interact.

The first component may be applied as a continuous layer over the metal film; if the metal film is discontinuous, different areas of metal may have different sensitive materials applied thereto, or they may all have the same sensitive material attached. With continuous metal layer, the first component may be applied all over, or in separate smaller areas which can be individually scanned as the line or point of incidence passes over them. In this way, a large number of tests can be carried out, in effect, simultaneously. Such smaller sensitive areas may all comprise the same sensitive material, or it may be different, so that a single sample can be subjected to several different tests at a time. The sample may be arranged to flood over the whole area, or may be channelled so as to come into contact with only selected sensitive areas. This enables several samples to be tested simultaneously and/or a reference test on a control sample to be carried out simultaneously with that on a main sample.

If raster (line) scanning is used, it is preferred to position such sensitive areas under the path of the point or line of incidence so that, as scanning takes place, the tests can be monitored by reference to the output of the radiation detector which can be related to the particular X-Y position of the test.

The metal film material is commonly silver or gold, usually applied by evaporation. The film needs to be as uniform as possible in order to cater for minute movement in the point of incidence of the incoming beam. It is assumed that a structured metal film will give the best resonance and there are various ways in which the transparent plate to which it is applied can be pretreated to improved the performance of the metal film and in particular to control the natural tendency of such films to form discontinuous islands:

1. Immersion in molten metal nitrates and other molten salts. This has the effect of introducing ions into the surface in a manner which can be structured and which can act as foci for island formation.
2. Ion bombardment of cold or hot glass to introduce nucleating sites. The removal of the more mobile ions has been demonstrated to reduce the thickness at which the evaporated film becomes continuous.
3. Electroless plating or electroplating over lightly evaporated films (0 to 100 angstroms thick). Electroless plated films survive to a greater thickness than evaporated films and could form more stable nuclei for subsequent coating.
4. Evaporating onto electroless plated films. The electroless plated films have a stronger tendency to an island structure and to bigger islands with greater spacing than evaporating films. This could be of advantage in tuning to light of a prescribed wavelength.

Coating performance can also be improved by:
1. Controlling the surface temperature of the transparent plate during coating. Using a higher temperature substrate increases the islands' size and the spacing between them and conversely.
2. Evaporating in the presence of a magnetic or electrostatic field or electron emission device to control the ion content of the vapour stream. The state of charge of the substrate is know to affect the island structure.
3. Controlling the angle of incidence of the evaporated vapor stream relative to the surface of the plate. The mobility of the evaporated atoms and hence their ability to form bigger islands is greater when the momentum of the atoms relative to the glass surface is increased.

BRIEF DESCRIPTION OF THE DRAWINGS

In order that the invention may be better understood, some embodiments thereof will now be described by way of example only and with reference to the accompanying drawings in which.

DETAILED DESCRIPTION OF THE PREFERRED EMBODIMENTS

Figure 2:
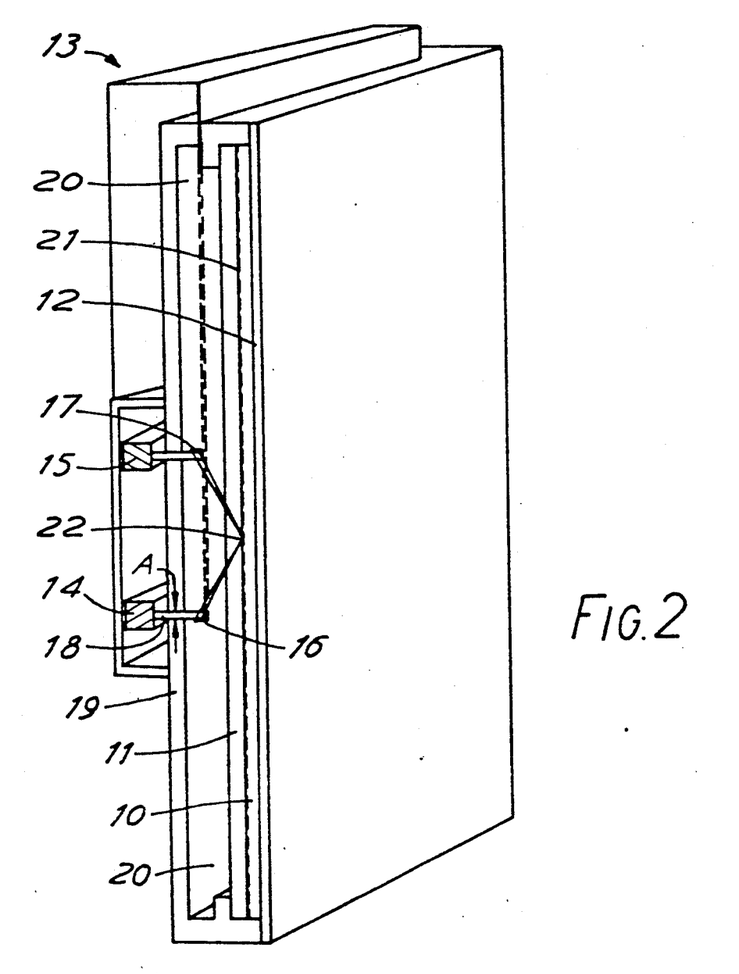
FIG. 2 is a diagrammatic perspective view of a planar SPR sensor constructed in accordance with the invention.

Referring firstly to FIG. 2 there is shown a conventional vertically oriented electrophoresis apparatus comprising an electrophoresis gel 10 sandwiched between a pair of plates 11, 12. Such apparatus is well known, and will not be described in detail here. Electrodes (not shown) are provided in order to produce a vertical current flow through the gel. Formed along the top edge of the gel are a plurality of spaced wells (not shown), each of which carry a separate sample to be analyzed. Such samples may, for example, comprise the sub-samples which are produced when a DNA sample to be analyzed is fragmented in a manner described above to give the four different sub-samples required to enable identification of the four bases. One sub-sample is placed in each well and a potential is applied across the electrodes. During electrophoresis, the gel acts as a skeletal foam in which are formed pores through which the material of the samples can pass under the influence of the electric current. The action of the current causes the fragments to migrate downwards through the gel, forming a distinct track emanating from each well, and travelling through the gel. The fragments formed by the fragmentation process tend to travel through in groups of identical length, those groups containing the shorter length fragments tending to travel faster through the gel than those containing the longer length fragments. As a result, the different groups tend to be bunched up near the top of the gel—i.e. nearest the well—but as they travel down the gel they become spread out because they are travelling at different speeds. The progress of the fragments through the gel is, of course, invisible to the naked eye but dyes can be used to enable visual monitoring of progress.

The SPR detector for monitoring the progress of the electrophoresis is mainly mounted on a frame 13 which is slidable vertically with respect to the gel to effect scanning, as will be explained. The SPR detector comprises a light source 14 (for example, a laser), light detector 15 and concave reflectors 16, 17 all of which move up and down with the frame. The output from the light source is passed through a slit (not shown) or the equivalent to produce a flat planar beam 18 extending horizontally—i.e. transversley across the expected tracks within the gel. Only the end of the beam is shown. It will be noted that the beam 18 has moderate depth A in the vertical direction.

Upon leaving the light source, beam 18 passes orthogonally through a plate 19 defining, with the plate 11, a chamber 20 in which the reflectors 16, 17 are situated. This chamber contains a liquid having the same refraction index as that of the plate 11 so that light passing across the boundary between chamber 20 and plate 11 at an angle is not refracted. Both plates 11 and 19 are made from transparent material.

Formed on that side of plate 11 which faces the gel is a metal layer in the form of a mosaic of silver dots 21 formed as an X-Y array. A thin layer of insulating material such as polyimide covers the mosaic to prevent the conductive gel from electrically shorting the dots. This thin layer does not affect the operation of the detector.

In operation, the light beam 18 from source 14 is applied to reflector 16 which is so shaped as to direct all of the light incident upon it to a single line 22 lying on that internal surface of the plate 11 against which the mosaic 21 is formed. The line 22 extends horizontally across the electrophoresis tracks and thus appears as a point in FIG. 2. The input light beam between reflector 16 and line 22 thus takes the shape of a solid wedge of light, the two converging lines shown in the drawing representing the outer boundary of the converging solid beam.

The angle of incidence of the incoming beam at the line 22 is such as to cause total internal reflection of the beam, the resultant internally reflected beam diverging from the line 22, again with a wedge shape, to be incident on the reflector 17 where the output light is reflected into a parallel beam which enters the detector 15. The detector 15 is connected to external circuitry (not shown) which analyzes the detector output.

The detector 15 comprises an array of separate sensitive areas extending horizontally across the gel in such a way that each detector monitors an individual silver dot in the horizontal (X) direction.

If conditions are correct and in particular if the range of angles spanned by the incident beam 18 is correct, then surface plasmon resonance will occur, this manifesting itself as a sharp dip in the intensity of the output beam as detected by the array detector 15 (see above). The effect of a change in the refractive index in the medium—in this case the gel 10—behind the plate 11 is to cause the angle of incidence at which surface plasmon resonance occurs to change. If the whole dip is being monitored by ensuring that the span of the angles of incidence of converging input beam 18 cover the resonant condition, then a change in refractive index in the gel 10 translates at the detector 15 into a rapid change in output intensity.

By this means, the passage of fragments down the gel during electrophoresis can be monitored by observing the change in refractive index which occurs as the bunches of fragments of identical length travel down the gel.

In order to obtain a real time analysis of the whole gel surface as electrophoresis proceeds, the frame 13 together with components 14 to 17 is vertically scanned up and down with respect to the gel by means not shown. The scanning movement of the frame 13 is synchronized with the detector output so that the associated circuitry can tell at any one time which line of dots in the vertical (Y) direction it is looking at. The scanning speed need only be relatively slow since the changes which occur during electrophoresis are themselves slow.

Alternative optical geometries (not shown) may be envisaged where the incoming wedge-shaped light beam is reflected off a rotating polygon similar to that used in document scanners and copiers to give a horizontal line focus on the silver dots.

The silver dots may be applied by any of the methods outlined above, or may be provided in the form of a throw-away sheet of silver dots on a disposable membrane which is optically coupled to the plate 11.

The apparatus shown in FIG. 2 may also be used to analyze the pattern of fragments in the gel after the electrophoresis test has been completed, rather than monitoring during electrophoresis, as described above. This obviously introduces a delay in obtaining the results, but may be preferred in some circumstances. The use of this technique also offers a way of improving the sensitivity of the system by drying out the gel after electrophoresis is completed. This is achieved by running the electrophoresis test in the normal way, and then removing plate 12 to expose that surface of the gel remote from silver mosaic layer 21 to the air. The gel thus dries out and shrinks: in so doing a typical 100 micron thick get might reduce in thickness to as little as 4/5 microns if all the water is evaporated, and this thus concentrates all the DNA fragments into the 4 or 5 microns closest to the silver mosaic layer. In this way, the sensitivity is improved because the concentration of fragments which the SPR detector is effectively able to look at is greatly increased.

Other ways of encouraging the fragments to move towards the silver layer might be conceived—for example the electric current flow could be distorted to cause the fragments to move towards the silver film layer, thus increasing sensitivity.

Figure 3:
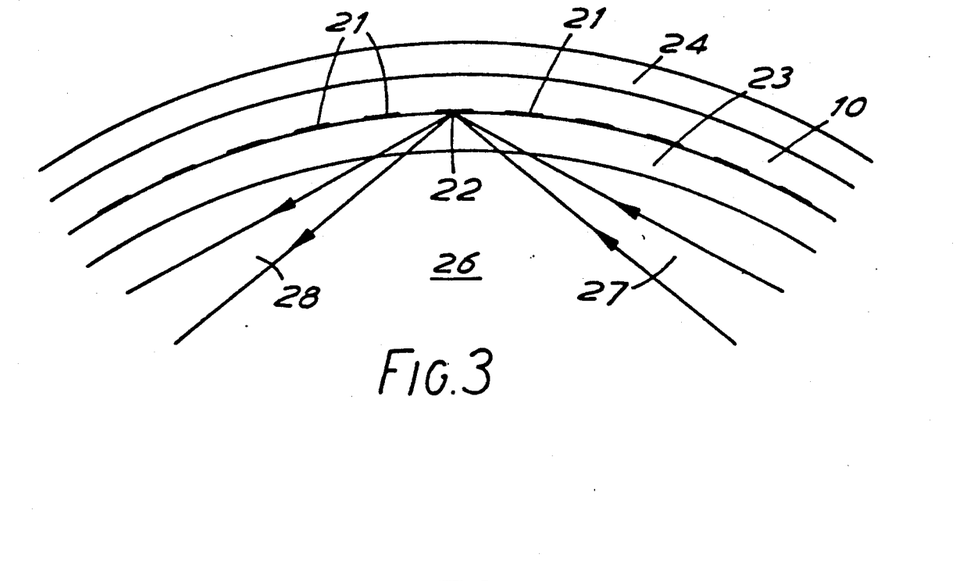
FIG. 3 is a diagrammatic partial plan view of a cylindrical SPR sensor constructed in accordance with the invention.
Figure 4:
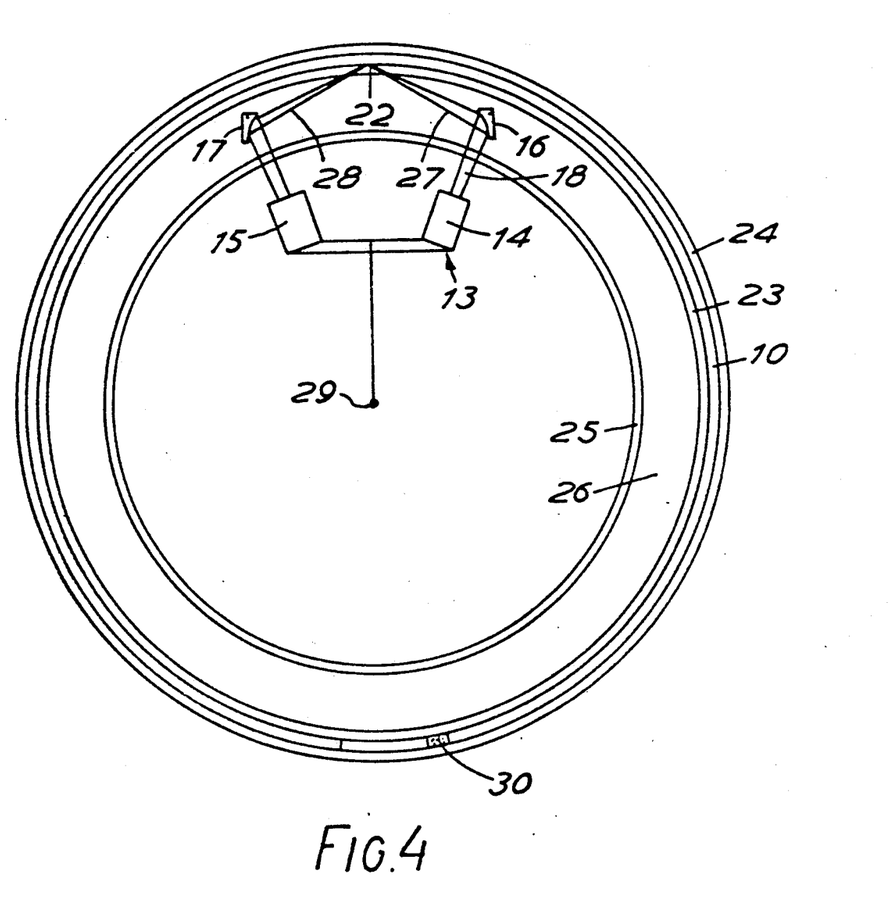
FIG. 4 is a view similar to FIG. 3, but showing the entirety of the apparatus on a smaller scale.

Referring now to FIG. 3 and 4 a second embodiment is illustrated, in which the gel 10 is confined in the annular gap between two concentric cylinders 23, 24 at least the inner (23) of which is made of transparent material. A further concentric cylinder 25, also of transparent material, lies inwardly of cylinders 23 and 24 and is equivalent to the plate 19 of the previous embodiment. An annular chamber 26 defined between cylinders 23 and 25 contains a liquid having a refractive index equal to that of cylinder 23. As before the main components of the SPR detector are mounted on a frame 13 which in this case is rotatably mounted about the center axis 29 of the cylinders. The light source 14, array detector 15 and reflectors 16, 17 all move with the frame. The reflectors 16, 17 are mounted within the index-matched fluid in the chamber 26 so that the wedge-shaped beams, shown under references 27 (input) and 28 (output) do not undergo refraction as they pass at an angle across the boundary between the chamber 26 and the cylinder 23. Extensive refraction of the input beam 18 from light source 14 is achieved by directing the output light beam in a radial direction. Similar comment applies to the beam entering the array detector 15.

The inner cylinder 23 is formed, on its outer surface, with a mosaic of silver dots in the same manner as previously described. In this case, the rows of dots extend axially and azimuthally of the cylinders. An insulating layer covers the dots to isolate them from the conductive effect of the gel.

A plurality of separate wells are arranged in the gel along a line parallel with the axis 29. One of these wells is indicted diagrammatically under reference 30. Each well contains a separate sample or sub-sample for analysis. Electrodes (not shown) are arranged to cause an electric current flow through the gel in an azimuthal direction. During electrophoresis the fragments from the individual wells migrate in an anticlockwise azimuthal motion around the gel, forming a plurality of circular tracks, one extending from each well, in the manner described above.

As electrophoresis proceeds, progress is monitored by rotating the frame 13 to scan the whole area of the electrophoresis gel. As before, the scanning rate does not need to be high in view of the relatively slow progress of the electrophoresis.

Figure 5:
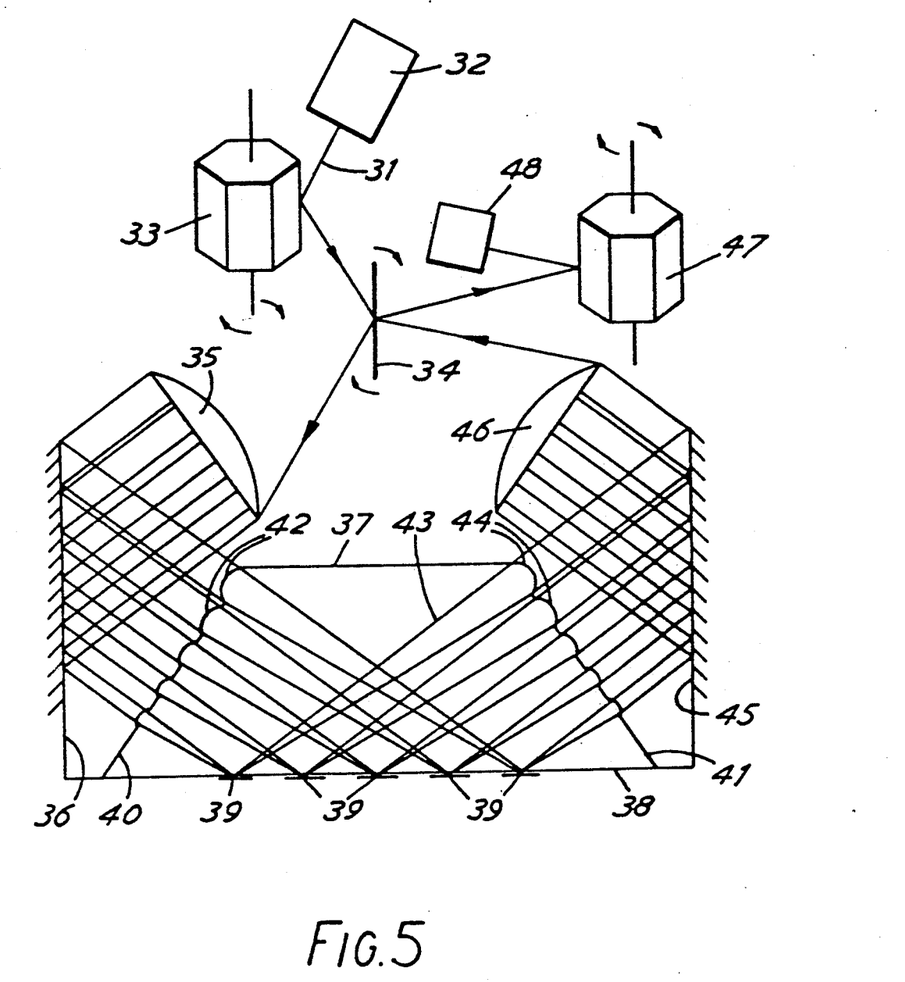
FIGS. 5 and 6 are diagrammatic views of an alternative embodiment of the SPR sensor of the invention.
Figure 6:
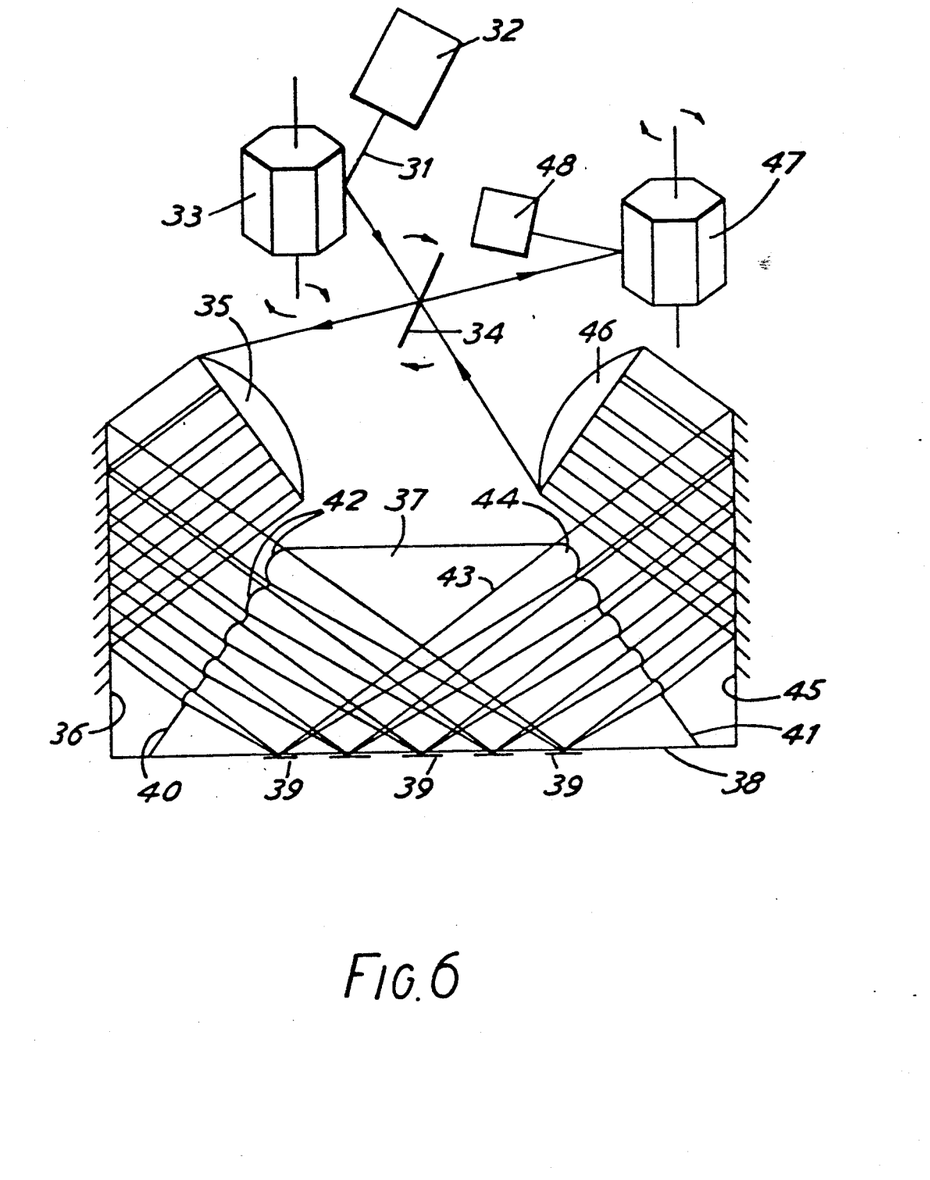
Figure 7:
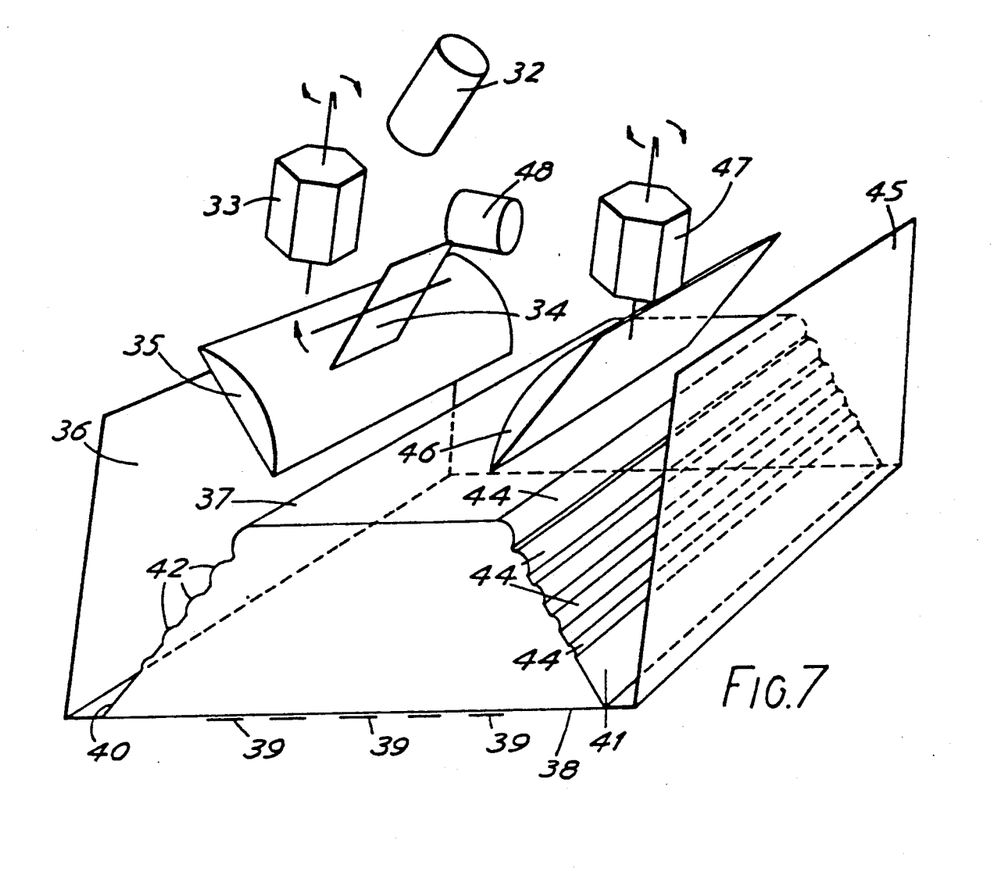
FIG. 7 is a perspective view of the apparatus of FIGS. 5 and 6.

Referring now to FIGS. 5, 6 and 7 there is shown a second embodiment of the invention in which scanning takes place by movement of mirrors.

A pencil light beam 31 from a light source 32 (for example, a laser) is reflected off a polygonal drum mirror 33 then off a double-sided rotating mirror 34 and enters a plano-convex lens 35. As the mirror 34 rotates, the reflected beam scans across the input convex face of lens 35 in the plane of the drawing. Collimators (not shown) are preferably used to reduce stray light after the reflected beam has left the lens 35. By way of illustration, FIGS. 5 and 6 show, respectively, the beginning and the end of the sweep of the reflected beam across the lens 35. The lens 35 is such as to bring all the reflected beams into lparallel paths so that, whatever the instantaneous angle of mirror 34 the output from lens 35 is always in a particular direction. This is represented in FIGS. 5 and 6 by a series of parallel lines although, of course, only a single beam is passing at any one instant of time. The beam leaving the lens 35 is incident on a planar mirror 36 which reflects the beam into a prism 37 made of transparent material such as glass. As will be clear from FIG. 7, the plano-convex lens 35, mirror 36, and prism 37 are elongate in a direction orthogonal to the plane of FIGS. 5 and 6. the reason for this will become apparent.

The prism 37 has a planar surface 38 on which is formed a metal layer in the form of a mosaic of silver dots 39 formed as an X-Y array. As shown, the X-Y array may, for example, comprise 5 rows and 10 columns—i.e. 50 dots in all. Illustrated in FIGS. 5 and 6 are the dots 39 of one of said 10 columns.

On the remote side of the dots is a medium whose refractive index is to be measured. For example, as in the previous embodiment, this medium could take the form of an electrophoresis gel. If the medium is electrically conductive, then a thin insulating layer may be applied between the dots and the medium to prevent electrical interaction between the dots. Alternatively, the medium may take the form of a layer of specific or non-specific sensitive material, such as a layer of antibodies which is to react with a sample to be tested (not shown). The sensitive layer may be applied individually to each dot of the mosaic, or may be applied over the whole surface, possible with a thin electrically insulating layer between it and the mosaic if necessary. As with the previous embodiment, the metal layer may be a continuous layer, the surface being notionally broken down into pixels by electronic means, as will be explained later.

The sides 40, 41 of the prism 37 are angled, as shown, and the mirror 36 is arranged so that light reflected off it is incident orthogonally to the general plane of side 40. The side 40 is formed with a set of protruding convex elements 42 extending along the length of the prism. Each of these elements is associated with one row of dots 39 extending orthogonally to the plane of FIGS. 5 and 6 and acts to focus light passing across it to a point approximately centrally of the row of dots. Thus, as the mirror 36 rotates, the light moves across each element 42 in turn. In between the elements, the prism surface is blackened to prevent stray light from entering and increasing the noise level.

As the light beam passes across each element 42, it is refracted to the aforementioned central point with a varying angle of incidence. This range covers those angles that give rise to surface plasmon resonance at the surface 38. The resultant internally reflected beam 43 passes through a corresponding one of a similar plurality of convex elements 44 formed on the side 41 of the prism. A planar mirror 45 and plano-convex lens 46 corresponding respectively to mirror 36 and plano-convex lens 35 act to bring the internally reflected beam onto the reflective rear side of mirror 34 at which it is reflected, via a second polygonal drum mirror 47, to a light detector 48. Surface plasmon resonance occurring at surface 38 is viewed as a dip in the intensity of the internally reflected beam 43, as measured at the detector 48. As the incident light beam scans across those angles of incidence which result in surface plasmon resonance occurring, the whole dip can be viewed by analysis of the output signal of the detector 48. As the mirror 34 rotates, the light is applied to the elements 42 one by one and is brought to a focus on the dots 39, likewise one by one. However, only the single column of dots 39 which are in the plane of FIGS. 5 and 6 will be covered. To cover the remaining columns of dots 39 the polygonal drum mirror 33 is rotated by a small amount for each 180° rotation of the mirror 34. While the input beam is being scanned across the lens 35 the mirror 33 is stationary. In between scans, however, the mirror 33 is stepped around by a small angle to thereby cause the input beam, on its next scan across the lens 35, to be incident on the next adjacent column of dots. In this way, all the dots can be covered by incrementing the mirror 33 around for each 180° of rotation of mirror 34 (mirror 34 is double-sided). For this purpose, mirror 33 need only be a planar mirror, but the use of a polygonal drum mirror is mechanically advantageous because it eliminates the large return movement which is necessary between each full field scan—instead of returning through a large angle to its start position, the mirror is simply turned to the next facet, and the process repeated. Although a six-sided mirror is shown, this has no particular significance and different numbers of sides could be used. On the output side, polygonal drum mirror 47 is step rotated in synchronism with mirror 33 to bring the incoming beam to the detector 48 from whichever dot 39 it has been reflected.

It will be appreciated that FIGS. 5, 6 and 7 are very diagrammatic in nature. For the sake of clarity, details of supporting structure, drive motors etc., are not given since they will be apparent to those skilled in the art. Also, the dots 39 are not spaced from surface 38, as shown, but are positioned directly on the surface.

The electrical output from the detector 48 is passed to an associated computer or the equivalent (not shown) so that the resultant signals can be analyzed with reference to the rotation of the mirrors 33, 34 and 47. In practice, of course, the rotation of the three mirrors will be synchronized and appropriate synchronizing signals passed to the computer so that the detector knows what it is looking at.

Although in all of the above described embodiments the metal layer is described as being in the form of a mosaic of metal dots, this is not essential, and the metal layer could take the form of separate stripes or even a continuous layer.

Figure 8:
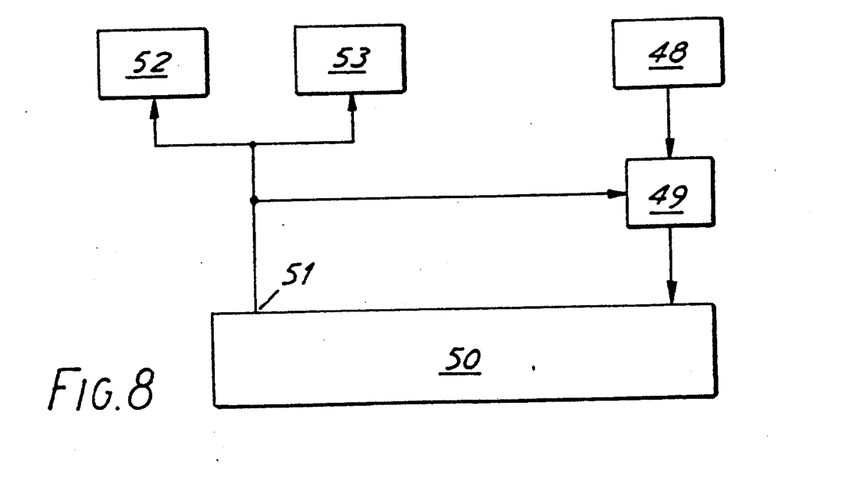
FIG. 8 is a block diagram of one example of the manner in which the output of the SPR detector can be synchronized with the mirror motion in the apparatus of FIGS. 5 to 7.

In the latter case, the area being examined is still divided into small cells or pixels for the purpose of analysis, but this division is carried out electronically, rather than, in effect, mechanically. To achieve this, the output signal from the detector must be synchronized with the mechanical scanning movements so that the instantaneous output from the detector can be correctly related to a particular X-Y position on the area being scanned. FIG. 8 illustrates, for the apparatus of FIGS. 5 to 7, one way of achieving this.

Referring to FIG. 8, the output signal from the detector 48 is gated in a gate 49 before being passed to a computer 50 for analysis. The clock output 51 from the computer is used to control the opening of the gate and also to control the drive mans 52 for the mirror 34 and the drive means 53 for the mirror 33 (mirror 47 moves in synchronism with mirror 33). Thus, if we take the previous example of 50 dots in an array of 5 rows and 10 columns, it is assumed that each of the 5 rows corresponds to one of the elements 42/44 and that the drum mirrors 33/47 rotate in 10 small steps, each step being sufficient to move the incident light beam to the next column. When all of the 10 columns have been scanned, the mirrors 33, 47 move on to the next facet, at an angle suitable to bring the incident light back to the start so that the scanning can begin again. In FIG. 8, the clock pulses are arranged to open the gate 49 ten times for each single rotation o mirror 34, this value of ten corresponding to 2 ×5, bearing in mind that the mirror is double sided, and therefore causes two scans of the input light for each rotation. The clock pulses also control rotation of the drum mirrors 33, 47, for example by means of respective stepper motors, to step rotate by an amount sufficient to move the incident light to the next column each time the mirror 34 rotates through 180°. Thus, for each clock pulse, the gate 49 is opened 50 times, the mirror 34 rotates 5 times, and the drum mirrors 33/47 step rotate 10 times. This completes one scan of the area, and the drum mirrors 33/47 are now stepped on to the next facet, and the process repeated. The pulses applied to gate 49 are such as to open the gate for a period sufficient to allow through the complete SPR dip resulting from the scan across each of the 50 spots. Thus, for each scan, we get 50 SPR dips resulting from each of the points at which the incoming beam is incident, and this signal can be analyzed by the computer to enable the SPR analysis of the whole area. Repeated scans of the area enable changes with time to be studied.

It will be seen that, by relating the movement of the beam with the output of the detector, such as shown in FIG. 8, a continuous metal layer can be employed in place of the mosaic of dots 39. In certain circumstances, it may be necessary or desirable to incorporate thin insulating film (see above) over the metal layer so that the medium beign measured is electrically isolated from the metal layer. This would be desirable where, for example, the medium takes the form of an electrophoresis gel which relies for its operation on the passage of current therethrough. If no insulation were present, a continuous metal layer would make it virtually impossible to pass the necessary current through the gel to make the electrophoresis apparatus function.

We claim:
1. Sequencing apparatus comprising: means for analyzing a sample containing fragments which has been subjected to electrophoresis whereupon the fragments have been distributed in a pattern within the electrophoresis medium; and means, including a detector, for detecting the pattern of fragments distributed within the electrophoresis medium by inducing surface plasmon resonance at a boundary of said medium and by utilizing the phenomenon of such surface plasmon resonance to monitor the pattern of fragments by virtue of the change in refractive index which occurs in those parts of the electrophoresis medium in which fragments are present.

2. Sequencing apparatus as claimed in claim 1, wherein the detector means is moveable with respect to the electrophoresis medium, and further comprising means for moving the detector means over the medium in a scanning direction.

3. Sequencing apparatus as claimed in either one of claims 1 or 2, wherein the electrophoresis medium is a gel.

4. Sequencing apparatus as claimed in either one of claims 1 or 2, wherein said detector means further includes a source of electromagnetic radiation, a block of transparent material, a thin film of metal disposed over one surface of of said block and against which film is positioned the electrophoresis medium with the metal film interposed between the electrophoresis medium and the transparent block, and means for directing the electromagnetic radiation from the source into the transparent block in such a way that the radiation is subject to total internal reflection at said one surface of the block, said detector being a radiation detector for monitoring the intensity of the radiation which is totally internally reflected.

5. A method of sequencing comprising subjecting a sample containing fragments to electrophoresis to thereby distribute the fragments along the electrophoresis medium according to their size and/or charge and detecting, using the phenomenon of surface plasmon resonance, the pattern of distribution of the fragments within the medium by virtue of the change in refractive index which occurs in those parts of the medium in which fragments are present.

6. A method as claimed in claim 5, wherein the step of detecting is carried out by moving a detector across the medium in a scanning direction.

7. A surface plasmon resonance sensor comprising: a source of electromagnetic radiation; a block of transparent material; a thin film of metal disposed over one surface of said block; a medium to be tested disposed against said metal film with the metal film interposed between the medium and the transparent block, said medium comprising first and second components of a biological, biochemical or chemical interaction, said first component being attached to said metal film in a plurality of areas isolated from one another, and said second component being a sample to be analyzed disposed in contact with said first component; means for directing the electromagnetic radiation from said source into the transparent block in such a way that the radiation is subject to total internal reflection at said one surface of the block; scanning means for scanning the radiation beam incident on said surface sequentially across said areas in order to obtain a two-dimensional representation of any variation in the refractive index across said areas so that the interaction between said second component and said first component in each of said areas can be monitored in sequence; and radiation detector means for monitoring the intensity of the radiation which is totally internally reflected.

8. A sensor as claimed in claim 7, and further comprising a membrane of dielectric material positioned against said one surface of the block of transparent material, and wherein said metal film is applied to that surface of the membrane remote from said block so that the membrane is interposed between the block and the metal film, the refractive index of said block being higher than that of said membrane such that total internal reflection takes place at the interface between the block and the membrane.

9. A sensor claimed in claim 7, wherein said metal film is disposed directly against said one surface of the block.

10. A sensor as claimed in any one of claims 7 to 26, wherein said metal film comprises a plurality of discontinuous areas of metal film.

11. A sensor as claimed in claim 10, wherein said metal film is a two-dimensional array of dots of metal film.

12. A sensor as claimed in any one of claims 7-9 and 11, wherein said medium is an electrophoresis medium forming part of an electrophoresis apparatus for the sequencing of macromolecules.

13. A sensor as claimed in claim 10, wherein said medium is an electrophoresis medium forming part of an electrophoresis apparatus for the sequencing of macromolecules.

14. A surface plasmon resonance sensor comprising: a source of electromagnetic radiation; a block of transparent material; a thin film of metal disposed over one surface of said block; a medium to be tested disposed against said metal film with the metal film interposed between the medium and the transparent block; means for directing the electromagnetic radiation from the source into the transparent block in such a way that the radiation is subject to total internal reflection at a point on said one surface of the block; scanning means for scanning the radiation beam incident on said surface as a pattern of sequentially and closely laid out parallel lines in each of two dimensions across said surface in order to obtain a two-dimensional representation of any variation in the refractive index across said medium; and radiation detector means for monitoring the intensity of the radiation which is totally internally reflected.

15. A sensor as claimed in claim 14, and further comprising a membrane of dielectric material positioned against said one surface of the block of transparent material, and wherein said metal film is applied to that surface of the membrane remote from said block so that the membrane is interposed between the block and the metal film, the refractive index of said block being higher than that of said membrane such that total internal reflection takes place at the interface between the block and the membrane.

16. A sensor claimed in claim 14, wherein said metal film is disposed directly against said one surface of the block.

17. A sensor as claimed in any one of claims 14 to 16, wherein said metal film comprises a plurality of discontinuous areas of metal film.

18. A sensor as claimed in claim 17, wherein said metal film is a two-dimensional array of dots of metal film.

19. A sensor as claimed in any one of claims 14-16 and 18, wherein said medium is an electrophoresis medium forming part of an electrophoresis apparatus for the sequencing of macromolecules.

20. A sensor as claimed in claim 19, wherein said medium is an electrophoresis medium forming part of an electrophoresis apparatus for the sequencing of macromolecules.

21. A surface plasmon resonance sensor comprising: a source of electromagnetic radiation; a block of transparent material; a thin film of metal disposed over one surface of said block; a medium to be tested disposed against said metal film with the metal film interposed between the medium and the transparent block; means for directing the electromagnetic radiation from the source into the transparent block in the form of a wedge of radiation in such a way that the radiation is subject to total internal reflection in a line of incidence at said one surface of the block constituting an apex of the wedge; scanning means for scanning the line of incidence across the entirety of said surface in a direction orthogonal to the length of said line in order to obtain a two-dimensional representation of any variation in the refractive index across said medium; and radiation detector means for monitoring the intensity of the radiation which is totally internally reflected.

22. A sensor as claimed in claim 21, and further comprising a membrane of dielectric material positioned against said one surface of the block of transparent material, and wherein said metal film is applied to that surface of the membrane remote from said block so that the membrane is interposed between the block and the metal film, the refractive index of said block being higher than that of said membrane such that total internal reflection takes place at the interface between the block and the membrane.

23. A sensor claimed in claim 21, wherein said metal film is disposed directly against said one surface of the block.

24. A sensor as claimed in any one of claims 21 to 23, wherein said metal film comprises a plurality of discontinuous areas of metal film.

25. A sensor as claimed in claim 24, wherein said metal film is a two-dimensional array of dots of metal film.

26. A sensor as claimed in any one of claims 21-23 and 25, wherein said medium is an electrophoresis medium forming part of an electrophoresis apparatus for the sequencing of macromolecules.

27. A sensor as claimed in claim 24, wherein said medium is an electrophoresis medium forming part of an electrophoresis apparatus for the sequencing of macromolecules.

28. A surface plasmon resonance sensor comprising: a source of electromagnetic radiation; a block of transparent material; a thin film of metal disposed over one surface of said block; a medium to be tested disposed against said metal film with the metal film interposed between the medium and the transparent block; means for directing the electromagnetic radiation from the source into the transparent block in such a way that the radiation is subject to total internal reflection at said one surface of the block; scanning means for scanning the radiation beam incident on said surface across said surface in order to obtain a two-dimensional representation of any variation in the refractive index across said medium; and radiation detector means for monitoring the intensity of the radiation which is totally internally reflected;

said source of electromagnetic radiation, said means for directing the electromagnetic radiation and said radiation detector means being integrated so as to constitute a first structure, said block of transparent material, said film of metal and said medium being integrated so as to constitute a second structure, said first structure being movably mounted to said second structure, and said scanning means for also effecting movement of said first structure relative to said second structure to scan the radiation beam across said one surface of the transparent block.

29. A sensor as claimed in claim 28, and further comprising a membrane of dielectric material positioned against said one surface of the block of transparent material, and wherein said metal film is applied to that surface of the membrane remote from said block so that the membrane is interposed between the block and the metal film, the refractive index of said block being higher than that of said membrane such that total internal reflection takes place at the interface between the block and the membrane.

30. A sensor claimed in claim 28, wherein said metal film is disposed directly against said one surface of the block.

31. A sensor as claimed in any one of claims 28 to 30, wherein said metal film comprises a plurality of discontinuous areas of metal film.

32. A sensor as claimed in claim 31, wherein said metal film is a two-dimensional array of dots of metal film.

33. A sensor as claimed in any one of claims 28-30 amd 32, wherein said medium is an electrophoresis medium forming part of an electrophoresis apparatus for the sequencing of macromolecules.

34. A sensor as claimed in claim 31, wherein said medium is an electrophoresis medium forming part of an electrophoresis apparatus for the sequencing of macromolecules.

35. A sensor as claimed in claim 28, wherein a liquid medium is provided against that surface of the block of transparent material through which the electomagnetic radiation enters the block.

36. A sensor as claimed in claim 35, wherein said liquid medium has a refractive index equal to that of said block.

37. A sensor as claimed in claim 35, wherein said means for directing the electromagnetic radiation is positioned within said liquid medium.

38. A sensor as claimed in claim 36, wherein said means for directing the electromagnetic radiation is positioned within said liquid medium.

39. A surface plasmon resonance sensor comprising: a source of electromagnetic radiation; a block of transparent material; a thin film of metal disposed over one surface of said block; a medium to be tested disposed against said metal film with the metal film interposed between the medium and the transparent block; means for directing the electromagnetic radiation from the source into the transparent block in such a way that the radiation is subject to total internal reflection at said one surface of the block; scanning means including at least one movable mirror for scanning the radiation beam incident on said surface across said surface in order to obtain a two-dimensional representation of any variation in the refractive index across said medium; and radiation detector means for monitoring the intensity of the radiation which is totally internally reflected.

40. A sensor as claimed in claim 39, wherein said scanning means comprises first and second moveable mirrors.

said first mirror being moveable to scan the radiation over said one surface in a first direction, and second mirror being movable to scan the radiation over said one surface in a second direction orthogonal to the first direction, drive means operatively connected to each of said mirrors for rotating said mirrors, and control means for controlling said drive means to rotate said second mirror by a small amount in a step-wise manner each time said first mirror has scanned once across the surface in the first direction so that the surface is scanned by a pattern of sequential and closely laid out parallel lines of radiation in each of two dimensions.

41. A sensor as claimed in claim 39, further comprising means for relating the movement of said at least one mirror with the output from said radiation detector means to enable a two-dimensional representation of the medium to be generated.

42. A sensor as claimed in claim 40, further comprising means for relating the movement of said mirrors with the output from said radiation detector means to enable a two-dimensional representation of the medium to be generated.

43. A sensor as claimed in claim 39, and further comprising a membrane of dielectric material positioned against said one surface of the block of transparent material, and wherein said metal film is applied to that surface of the membrane remote from said block so that the membrane is interposed between the block and the metal film, the refractive index of said block being higher than that of said membrane such that total internal reflection takes place at the interface between the block and the membrane.

44. A sensor claimed in claim 39, wherein said metal film is disposed directly against said one surface of the block.

45. A sensor as claimed in any one of claims 39, 43 and 44, wherein said metal film comprises a plurality of discontinuous areas of metal film.

46. A sensor as claimed in claim 45, wherein said metal film is a two-dimensional array of dots of metal film.

47. A sensor as claimed in any one of claims 39, 43, 44 and 46, wherein said medium is an electrophoresis medium forming part of an electrophoresis apparatus for the sequencing of macromolecules.

48. A sensor as claimed in claim 45, wherein said medium is an electrophoresis medium forming part of an electrophoresis apparatus for the sequencing of macromolecules.

49. Sequencing apparatus as claimed in claim 3, wherein said detector means further includes a source of electromagnetic radiation, a block of transparent material, a thin film of metal disposed over one surface of of said block and against which film is positioned said gel with the metal film interposed between the gel and the transparent block, and means for directing the electromagnetic radiation from the source into the transparent block in such a way that the radiation is subject to total internal reflection at said one surface of the block, said detector being a radiation detector for monitoring the intensity of the radiation which is totally internally reflected.

* * * * *